Figure 1:
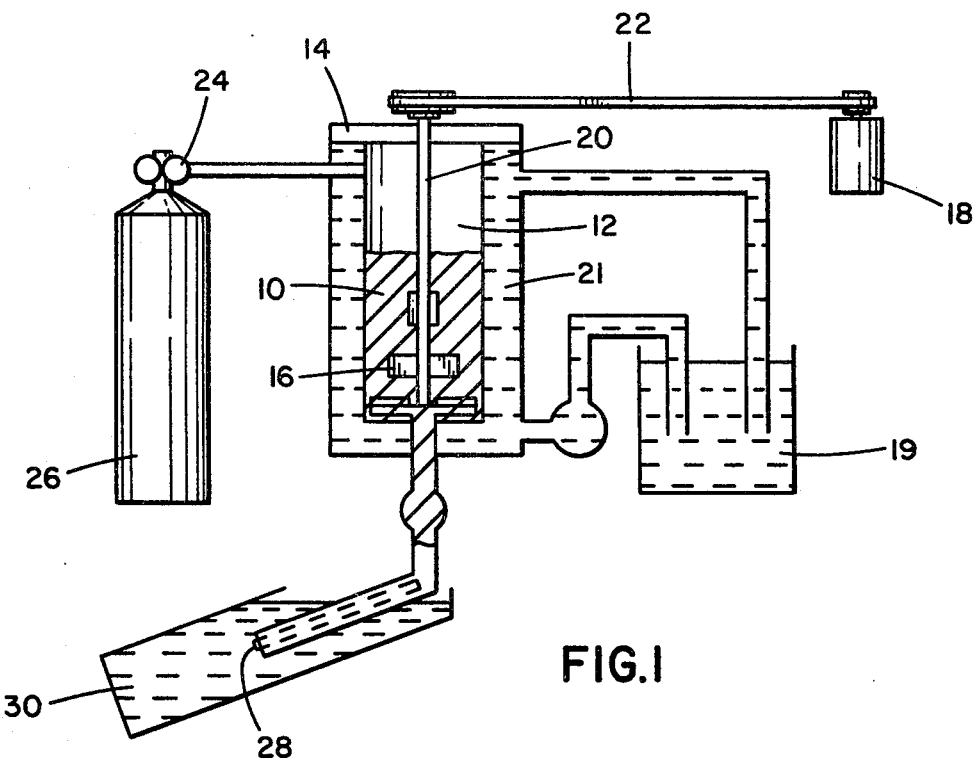

United States Patent [19]

Olson et al.

[11] 4,310,554

[45] Jan. 12, 1982

[54] PREPARATION OF CHEESE WITH MICROENCAPSULATED ENZYMES

[75] Inventors: Norman F. Olson, Madison, Wis.; Edward L. Magee, Jr., Plano, Tex.

[73] Assignee: Wisconsin Alumni Research Foundation, Madison, Wis.

[21] Appl. No.: 56,315

[22] Filed: Jul. 10, 1979

[51] Int. Cl.³ .................... A23C 19/02; C12N 11/04
[52] U.S. Cl. ........................................ 426/40; 426/38; 426/61; 426/89; 426/582; 435/174; 435/177; 435/182
[58] Field of Search ............... 426/89, 36, 38, 40, 426/61, 602, 582, 63, 601; 435/174, 177, 182

[56] References Cited

U.S. PATENT DOCUMENTS

| | | | |
|---|---|---|---|
| 3,223,532 | 12/1965 | Pinkalla et al. | 426/602 |
| 3,295,991 | 1/1967 | Cort et al. | 426/38 X |
| 3,561,975 | 2/1971 | Luebering et al. | 426/63 X |
| 3,650,768 | 3/1972 | Roberts | 426/36 X |
| 3,792,171 | 2/1974 | Little | 426/38 |
| 3,793,464 | 2/1974 | Rusch | 426/601 X |
| 3,889,004 | 6/1975 | Schmidt et al. | 426/582 X |
| 3,899,605 | 8/1975 | Schaap | 426/582 |
| 3,939,290 | 2/1976 | Terada et al. | 426/602 X |
| 4,172,900 | 10/1979 | Dooley | 426/38 |

FOREIGN PATENT DOCUMENTS

| | | | |
|---|---|---|---|
| 2602260 | 8/1977 | Fed. Rep. of Germany | 426/61 |
| 49-24235 | 6/1974 | Japan | 426/61 |
| 846777 | 8/1960 | United Kingdom | 426/602 |

*Primary Examiner*—David M. Naff
*Attorney, Agent, or Firm*—McDougall, Hersh & Scott

[57] ABSTRACT

A food processing component such as an enzyme extract is microencapsulated by mixing the food processing component in aqueous medium with an oleaginous material such as milk fat to form a water-in-oil emulsion and then dispersing the water-in-oil emulsion in an aqueous liquid such as milk to form a suspension of oleaginous microcapsules containing the food processing compoent. By forming microcapsules containing a cheese flavor producing enzyme extract in milk and making cheese curd from the milk, accelerated flavor production can be obtained during ripening of the cheese curd.

19 Claims, 2 Drawing Figures

PREPARATION OF CHEESE WITH MICROENCAPSULATED ENZYMES

This invention relates to a process for microencapsulation of substrates by way of a stable multiple phase emulsion and to products formed thereof. Microencapsulation allows for control and development of a capsule microenvironment where pH, ionic strength, enzymes and other substrates can be manipulated for optimum reaction efficiency in the processing of many materials and products.

The invention will be described with reference to the microencapsulation of enzymes for enhancing the ripening of cheese and the development of desired aroma and flavor, but it will be understood that the concepts of microencapsulation by way of stable multiple phase emulsion can be used, in accordance with the practice of this invention, in the processing of other dairy and food products.

Microencapsulation of curing agents in milkfat capsules has been found to be effective for concentrating the curing agent in an environment to accelerate reaction and to release such curing agents at a time and place where their effectiveness can be optimized, thereby markedly to increase the utility thereof and enable corresponding reduction in the amounts required to be utilized and/or markedly to increase the amount and rate of ripening and development of flavor and aroma.

Cheese ripening consists of complex enzymatic and chemical modifications of casein and milkfat and, to a limited extent, residual sugars in cheese. The reactions occur in sequential steps to produce the body, texture and balanced flavor of mature Cheddar cheese. Many investigators have attempted to accelerate or characterize the ripening process by incorporating into cheese various catalysts, such as selected enzymes, microbial cell free extracts, viable pregrown microbes and miscellaneous curing agents. Generally, these modifications have resulted in poor quality cheese presumably from an inability to control or coordinate the activity of the added catalyst in the normal events of cheese ripening. The inability of additives to accelerate satisfactory flavor development may have resulted, in part, from an improper spatial arrangement between the enzymes, microbes, and substrates.

An object of this invention resides in the microencapsulation to entrap enzymes, microbes or other substrates for release within a controlled locality, at a time and under conditions for optimization of reaction efficiency in the food and cheese processing industry.

Figure 2:
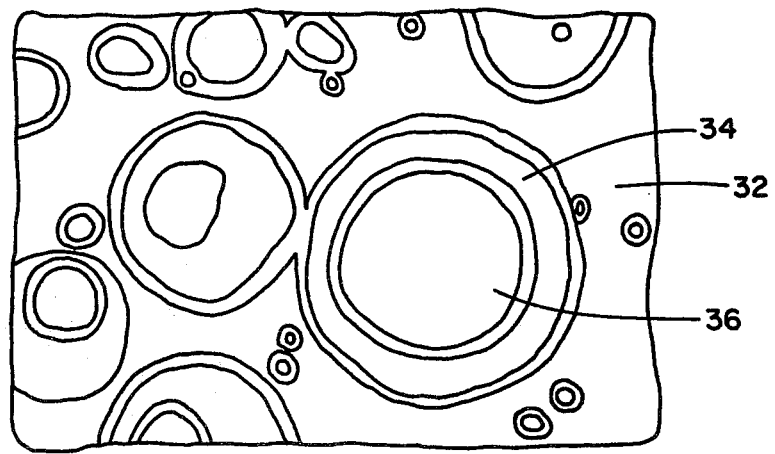

These and other objects and advantages of this invention will hereinafter appear and, for purposes of illustration but not of limitation, embodiments of the invention are shown in the accompanying drawings, in which:

FIG. 1 is a diagramatic sectional view of an apparatus which may be used in microencapsulation in accordance with the practice of this invention; and FIG. 2 is a photomicrograph of typical milkfat microcapsules of encapsulated carrier vacuoles dispersed in water.

Encapsulation can be designed for sustained release of the enzymes, microbes and other substrates to coincide with a particular event in cheese aging to enhance ripening and/or development of aroma and flavor. Microencapsulation of such agents or substrates enables retention and uniform distribution in the curd with minimal loss of the whey since, at the time of separation between the curd and the whey, the capsules represent a particulate component that is retained in the curd. Microencapsulation by way of multiple phase emulsion enables the capsules to be designed to fulfill the role of butterfat in cheese ripening and allow for the development of flavor even in low fat cheese.

Briefly described, the multiple phase emulsions of the water/oil/water (W/O/W) type are formed in accordance with this invention by two sequential emulsification steps. The water phase to be encapsulsted is first emulsified in oil containing a hydrophobic emulsifier to stabilize this initial W/O emulsion. This primary W/O emulsion is thereafter dispersed in a second aqueous phase which may or may not contain a hydrophilic emulsifier to stabilize the multiple phase emulsion capsules. The size of the capsules is determined in part by the emulsifier concentration and severity of the dispersion mechanism which can be stirring, shaking, extrusion or sonification.

Having briefly set forth the concepts of the invention, illustration will now be made of the microencapsulation of a cell free extract of *Streptococcus lactis. subsp. diacetilactis* and substrates with a view towards producing diacetyl plus acetoin in cheese.

EXAMPLE 1

Diacetyl is known to contribute to the aroma and flavor of fermented dry products from the metabolism of citrate by *Streptococcus lactis subsp. diacetilactis* and *Leuconostroc cremoris*. The biochemistry of diacetyl biosynthesis with *S. lactis subsp.diacetilactis* involved several sequential enzyme reactions when cell free extracts were incubated with pyruvate, thiamine pyrophosphate and magnesium ion which generated primarily acetoin and lesser amounts of diacetyl. The mechanism of diacetyl formation was the enzymatic conversion of pyruvate in two independent pathways to form acetyl-CoA and acetaldehyde-thiamine pyrophosphate. A condensation of these intermediates formed diacetyl. Acetoin resulted primarily by decarboxylation of α-acetolactate formed by condensation of pyruvate with acetyladehyde-thiamine pyrophosphate complex which was also derived from pyruvate. Decarboxylation of α-acetolactate to form acetoin occurred by a specific decarboxylase or spontaneously at a low pH. Acetoin was formed also by reduction of diacetyl by diacetyl reductase.

The conversion of pyruvate to diacetyl, acetoin or α-acetolactate by cell free extracts required the operation of a pathway with several enzymes, substrates and cofactors. This conjugated enzyme system was encapsulated to test the potential of the capsules to protect and maintain the activity of enzyme pathways in a favorable microenvironment inside the capsules by dispersing the capsules in an environment which may be unfavorable to unprotected enzymes. The capsules also served as a vehicle to incorporate curing agents into cheese.

MATERIALS AND METHODS

Growth Medium and Cell Disruption

All the medium components in citrate broth (Harvey, R. J. and Collins, E. B., 1961—Role of citritase in acetoin formation by *Streptococcus diacetylactis* and *Leuconostoc citrovorum*. J. Bacteriol. 82:954) except citrate and lactose were used to formulate the basal medium.

Designated amounts of lactose and citrate were added to this basal medium. *Streptococcus lactis subsp. diacetilactis* JV1 was obtained frozen from Marschall Division, Miles Laboratories, Madison, Wis. A single colony picked from Elliker agar (Difco, Detroit, Mich.) was grown for 12 hours at 32° C. in basal medium containing 2% citrate and 1% lactose. One drop of this culture was added to tubes of the same medium which were grown for 18 hours at 32° C. and held at −40° C. until used as stock cultures.

One to three liter quantities of cells were obtained by inoculating sterile broth of a designated composition at an amount of 10% (v/v) and incubating them for 18 hours at 32° C. Cells were concentrated by centrifugation. The cell pellet was washed in 200 ml of 0.1 M $KH_2PO_4$ buffer at pH 6.5 and resuspended in the same buffer in a volume approximately 1/20 the original culture fluid.

The cells were disrupted by pretreatment with lysozyme and sodium chloride followed by explosive nitrogen decompression. Cells were pretreated with 1.5 mg lysozyme/ml for 30 min. at 37° C. followed by addition of sodium chloride until the ionic strength was approximately 1.9 then held for 20 minutes at 37° C. The cells were transferred to a Parr cell disruption bomb and placed under pressure of 140.6 kg/cm² gauge with compressed nitrogen gas. After a 20 minute equilibration period, the cells were disrupted by reduction of pressure to atmospheric pressure. The cell homogenate was centrifuged at 6,800 xg, 15 minutes and the supernatant fluid containing the cell free extract was decanted and used immediately or frozen at −40° C. and used within six days after preparation.

MICROENCAPSULATION METHOD

Cell free extracts and/or substrates (hereinafter referred to as carrier) were encapsulated into milkfat capsules prepared by the following method. Frozen, unsalted butter was melted in free flowing steam and 200 g of milkfat was decanted into a beaker. The milkfat was maintained at 62° C. and 3 g of Glycomul TS (Glyco, Greenwich, Conn.) was added and held for 10 minutes until melted. Three grams of Span 60 (Ruger Chemical Company, Irvington, N.J.) was similarly added and melted. The milkfat-emulsifier mixture was transferred to a water bath at 37° C. and stirred at 250 rpm with a three bladed propeller, until the milkfat-emulsifier mixture was also 37° C. The stirring rate was increased to 500 rpm while slowly adding 40 ml of carrier consisting of a specified mixture of cell free extract and/or substrates. After 5 to 10 minutes of stirring, the emulsion was ejected into acidified skim milk at 15° C. to form the capsules. A Wagner ST350, airless sprayer with nozzle extension and 0.4 mm orifice was used to form the capsules.

Composition of the Encapsulated Carrier Made into Cheese

The cell free extract and substrate content of the capsules were varied to evaluate the performance of the capsules in cheese. The carrier composition of milkfat capsules added to skim milk and made into cheese are summarized in the following Table I. Most cheese trials were conducted with "intact" capsules. With intact capsules, no attempt was made purposely to disrupt the structural integrity of the capsules. Intact capsules contained the bacterial cell free extract and substrates which generated acetoin and diacetyl. This systemm in which intact capsules which generated diacetyl and acetoin in cheese was compared to control cheese made with the cell free extract and substrates which were not encapsulated but were dispersed in the milk before making into cheese. Dispersal of the enzyme and substrate was accomplished in two ways. The volume of an intact capsule emulsion was divided in half and one half left intact and made into cheese. The remaining half was heat treated at 45° C. for one minute to disrupt the capsules. This released the bacterial cell free extract and substrates into the milk from which cheese was made. These capsules were designated "broken" capsules. Since heating the capsules could inactivate the enzymes, another dispersion mechanism was used. The bacterial cell free extract and substrates were added directly to the milk which contained milkfat capsules with encapsulated buffer. This cheese is designated "unencapsulated". Two other cheeses were made from intact capsules containing only the cell free extract "CFE" or another cheese when intact capsules contained only the substrates, "substrate" cheese. The composition of the last two capsules tested if the cheese could supply the missing component required to generate acetoin and diacetyl.

TABLE I

Composition of carrier encapsulated in milkfat microcapsules formed in skim milk and made into cheese[a].

| Capsule label | Number of trials | Composition of carrier encapsulated in milkfat capsules[b] | | | Comments |
|---|---|---|---|---|---|
| | | cell free extract[c] | substrates[d] | buffer[e] | |
| intact | 6 | + | + | + | |
| broken | 2 | + | + | + | capsules destabilized by raising temperature to 45° C. for 1 minute |
| unencapsulated | 1 | − | − | + | milkfat capsules had encapsulated buffer. Cell free extract and substrates added directly to milk[f]. |
| CFE | 1 | + | − | + | |
| substrate | 1 | − | + | + | |

[a] 40 ml carrier added to 200 g milkfat + 6 g emulsifiers
[b] + indicates that the component indicated in column heading was included in carrier; − component in column heading not included in carrier
[c] 4 ml cell free extract + 36 ml buffer with or without substrates
[d] pyruvate, 29.9 mg/ml; thiamine pyrophosphate, 3.28 μg/ml; $MgSO_4$, 180 μg/ml, 0.1 M $KH_2PO_4$ buffer pH 6.5
[e] 0.1 M $KH_2PO_4$ buffer pH 6.5
[f] 1.3 ml cell free extract + 11.9 mls of (d) added to 4.000 kg skim milk + 445 gms of milkfat capsules with encapsulated buffer (e)

CHEESE MAKING

All of the cheese was made by a direct acidification procedure to avoid interference of the lactic starter culture in production of diacetyl and acetoin in cheese. Also, a low temperature was used to cook the curd to maintain integrity of the capsules. This resulted in a soft bodied, high moisture, low fat cheese. Composition of the cheese was similar to that previously reported for low-fat cheese (Hargrove, R. E., McDonough, F. E., and Tittsler, R. D. 1966-A new type of ripened low-fat cheese. J. Dairy Sci. 49:796).

In the cheese manufacturing procedure, 37.8 l of pasteurized skim milk at 5° C. was acidified with glacial acetic acid to pH 5.5–5.6 measured at 25° C. Four kilograms of acidified skim milk was weighed into three or four small rectangular pans and the temperature raised to 30° C. The quantity of capsules ejected into each lot of skim milk was controlled so that each lot of milk had approximately the same milkfat content. Commercial single strength rennet extract was added at one half to one third the normal amount of 88.7 ml/453.6 kg. At proper curd firmness, which was usually attained within 8 to 13 minutes after rennet addition, the curd was cut into 7 mm cubes with cheese knives. The curd was stirred in whey at 30° C. for 80 minutes, before the whey was drained and the curd piled and held at 30° C. for 20 minutes. It was then salted, hooped and pressed overnight at room temperature in forms under a 2.6 kg weight. The cheese was waxed and cured at 4° C. In a second experimentt, to evaluate the effect of the curd cooking temperature on the production of diacetyl and acetoin, all four lots of cheese were made with intact capsules containing the cell free extract and substrates. The milk with capsules was coagulated at 30° C., the curd was cooked to various temperatures and held for a specified time before the whey was drained and the curd piled, salted, hooped, pressed, waxed and cured.

ANALYSIS OF THE CHEESE

At specified times of aging, the cheese was analyzed for diacetyl and total diacetyl-acetoin. A 6 to 10 g plug of cheese was added to a test tube with a small volume of distilled water. The cheese was slurried with a rotor and strator probe homogenizer. Diacetyl and total diacetyl-acetoin were determined. For total diacetyl-acetoin, twice the specified volume of Westerfield oxidation reagents was added to assure complete oxidation of acetoin to diacetyl. Three samples were taken of each cheese with one sample being analyzed for diacetyl and the other two used for analysis of total diacetyl-acetoin. Cheese was analyzed for milkfat by a modified Babcock test and moisture by drying in a forced draft oven (Van Slyke, L. L and Price, W. V. 1952 Cheese. Orange Judd Publishing Co., New York, N.Y.

A broad comparison of total aroma development indicated cheese with the intact capsules produced approximately six times more total diacetyl-acetoin and diacetyl than the various control cheeses. In cheese containing intact capsules, there was a gradual rise in the concentration of total diacetyl-acetoin produced during the first days of aging which peaked between four to six days. This indicated diacetyl-acetoin production occurred within the capsules in the cheese rather than a result of formation from an instantaneous enzyme reaction when the enzyme was mixed with the substrate prior to encapsulation. The lower diacetyl levels in cheeses with intact capsules were expected from previous experiments with the cell free extract and substrates which were not encapsulated or added to cheese. Diacetyl production in cheese reached maximum levels within the first day of ripening which suggested diacetyl production was a result of an instantaneous enzyme reaction when the extract initially contacted the substrated. However, diacetyl production probably occurred while the capsules were pressed since the odor of this compound was not evident in the curd at hooping.

Aroma development in the control cheeses was almost nil. Diacetyl concentrations were below levels detectable by the assay procedure; total diacetyl-acetoin was measurable but extremely low. Cheese containing broken capsules contained approximately 0.9 to 1.3 $\mu$g total diacetyl-acetoin/gm cheese and the diacetyl was stable over the aging period. Correcting this value to account for presumed 40% loss of enzyme activity would increase the diacetyl-acetoin concentration to 3.2 $\mu$g/g cheese which is still four times lower than concentrations in cheese with intact capsules.

The unencapsulated cell free extract did not receive a heat treatment to potentially inactivate the extract. As a result, cheese made after the extract and substrates were added directly to milk offers the best control to compare the effect of adding intact capsules to increase diacetyl-acetoin in cheese. Cheese made with the unencapsulated cell free extract and substrates developed 1.3 $\mu$g diacetyl-acetoin/g cheese and undetectable levels of diacetyl. This value was six times less than the value of 8.3 $\mu$g diacetyl-acetoin/g cheese which developed in cheese with intact capsules which also developed 1.52 $\mu$g diacetyl/g cheese.

Substrate was required in the capsules for diacetyl-acetoin production since very little diacetyl-acetoin was produced in intact capsules with encapsulated cell free extract but not substrate. Substrate encapsulation without a cell free extract produced very little diacetyl-acetoin indicating no contamination occurred in these trails.

These results indicated that encapsulation of the multiple-enzyme system allowed maximum reaction between enzymes and substrates of the system to generate diacetyl and acetoin. In cheese in which the components were not encapsulated, the various enzymes, cofactors and substrates were too dispersed in the milk for sufficient interaction and also diffused from the curd into the whey. This resulted in low levels of diacetyl and acetoin being produced in the control cheeses.

EXAMPLE 2

Encapsulation of Glucose or Hydrolyzed Protein Solutions in Milk Fat Microcapsules Fresh milkfat was prepared by melting frozen butter in a covered glass beaker with free flowing steam. After siphoning off the aqueous phase, the remaining milkfat was decanted and used without further treatment.

The carrier phase to be encapsulated and used as a marker to determine the extent of encapsulation was a solution of D-glucose or Bacto-Peptone (Difco Laboratories, Detroit, Mich.) Solutions of both materials were prepared by dissolving in distilled water; the peptone solution was steamed 20 to 30 minutes to hasten dissolution.

The dispersion liquid, into which the carrier/milkfat emulsion was injected, was prepared by dissolving an amount of Tween 60 (Polyoxyethylene (20) sorbitan monostearate, Ruger Chemical Company, Irvington, N.J.) equal to 0.01% (w/v) of the final dispersion liquid in a small beaker of warm water. The Tween 60 solution was added to a tared vessel and tap water and ice were added until the desired volume and temperature was reached.

Preparation of Carrier in Milkfat Emulsion

Melted milkfat was weighed into a glass beaker and placed in a water bath at 62° C. and stirred at 250 rpm with a three blade propeller for 5 minutes. A specified weight of emulsifier(s) was added to the molten milkfat and stirred for 15 minutes. A designated volume of carrier with a defined solute content was slowly added to the milkfat-emulsifier mixture while stirring at 500 rpm. When the emulsion temperature reached 52° to 55° C., usually within 2 to 5 minutes after addition of the carrier, this emulsion was dispersed into the dispersion liquid with either of the two extrusion apparatuses.

Formation of Capsules with Pressure Vessel

Referring to FIG. 1, the prepared carrier in milkfat-emulsifier emulsion 10 was quickly transferred to pressure vessel 12. The chamber cover 14 was secured and the stirrers 16 were operated at approximately 100 rpm throughout the experiment by a variable speed motor 18 connected to the stirrer shaft 20 via belt 22. The temperature in the chamber is controlled by heat exchange liquid 19 circulated through the jacket 21 about the vessel 12. The regulator 24 for the cylinder 26 containing compressed nitrogen gas was opened to release nitrogen gas under pressure into the chamber 12. The headspace pressure produced the pressure differential for ejecting the carrier/milkfat emulsion when the chamber was opened to atmospheric pressure. Before capsule formation, 50 grams of emulsion was extruded through the orifice 28 and discarded to clear the ejection line. The orifice was immediately submerged into the prepared dispersion liquid 30 and further amounts of emulsion ejected to form the capsules. Approximately 75 to 100 g of carrier/milkfat emulsion was ejected into 1700 ml of dispersion liquid for each microcapsule emulsion. Generally, four individual microcapsule emulsions were made from one lot of emulsion in the chamber. If an interruption in the sequence of forming the capsules was necessary to change variables, such as orifice or pressure, 50 g of emulsion was extruded and discarded before the next group of capsules was formed. The maximum time period was 7 to 10 minutes from adding the emulsion to the chamber until the fourth batch of microcapsules was formed.

Photomicrographs of the capsules in FIG. 2 illustrate that the capsule configuration is a multiple phase emulsion. Plate A is an enlargement of a photomicrograph originally taken at a 1000X magnification of the capsules. The continuous phase 32 is water. The apparent ring 34 is a milkfat shell surrounding the encapsulated aqueous carrier vacuoles 36.

Temperature and the chemical type of emulsifier are important considerations for optimum emulsion stability. The percent encapsulation was highly dependent on the temperature of the dispersion liquid and the type of hydrophobic emulsifier blended in the milkfat. The emulsion of carrier/milkfat ejected into the dispersion liquid at a temperature of 16° C. resulted in better encapsulation than ejection into liquid at 25° or 35° C. The high melting point triglycerides in milkfat and possibly the added emulsifiers partially solidified when ejected into the dispersion liquid at 16° C. to form a rigid matrix to physically entrap carrier vacuoles within the milkfat capsules. Ejection into liquids below 16° C. produced large cylindrical capsules. This suggested that the carrier/milkfat emulsion emerged from the orifice as an elongated cylinder. The milkfat must be plastic enough for fluid turbulence to fracture the extruded milkfat into microcapsules.

The Hydrophile-Lipophile Balance (HLB) value of emulsifiers was used to select emulsifiers for use in the capsule formation process. Emulsifiers with a low HLB value in a range of three to six are hydrophobic emulsifiers and tend to stabilize W/O emulsions. Emulsifiers with a high HLB value in a range of 8–18 are hydrophilic emulsifiers and tend to stabilize O/W emulsions. HLB values are calculated by a number of ways, usually from either analytical or composition data of the emulsifier and essentially measure the relative hydrophilic and lipophilic tendency of bipolar emulsifier molecules.

Microencapsulation in multiple phase emulsions, in accordance with the practice of this invention, required a low HLB-hydrophobic emulsifier in the milkfat to stabilize the carrier/milkfat emulsion. This emulsion was dispersed in an aqueous phase containing a high HLB-hydrophilic emulsifier for adsorption to the milkfat-water interface to stabilize the capsules against coalescence.

Considering the dual emulsion character of the capsules, the stability of the carrier/milkfat emulsion determined the encapsulation efficiency of the carrier. Various nonionic, low HLB emulsifiers were tested for their effect on formation of microcapsules.

Phospholipid emulsifiers have an ionic moiety which increases the HLB value to favor O/W emulsions. Phospholipids were blended with Span 60 in milkfat to give the emulsifier blend an intermediate HLB. Lecithin and Emphos D70-31, when dissolved in milkfat, noticeably increased the milkfat viscosity. The mode of capsule stabilization probably is based on this physical property of increasing the milkfat viscosity particularly in the dispersion liquid at 16° C. Similar results were obtained where the rate of benzoic acid released from sunflower oil capsules was retarded by high HLB value emulsifiers which also increased the emulsion viscosity (Minkov, E., Docharov, D., Michailova, S., Bogdanova, Kassarova, M., and Kodurova, K.—1974—Some biopharmaceutical studies of emulsions of the O/W type. Pharm. Ind. 36(6):446).

Triglycerol monostearate (HLB 4.0) was blended with Span 60 (sorbitan monostearate) in milkfat and resulted in good encapsulation. The high melting point of this emulsifier, derived primarily from the stearate moiety, would enhance milkfat viscosity in dispersion liquid at 16° C.

Span 60 was blended with other low HLB emulsifiers of the sorbitan ester composition. Span 60 was blended with either Glycomul TO (sorbitan trioleate, HLB 1.8) or Glycomul TS (sorbitan tristearate, HLB 2.1) and both blends in milkfat encapsulated 80 to 90% of the glucose solution. The encapsulation success with the sorbitan triesters may be related to a number of their properties. The sorbitan triesters had the lowest HLB values of all the emulsifiers evaluated. In addition, sorbitan triesters are bulky and occupy more interfacial area per molecule than corresponding sorbitan monoesters as determined from film compression and surface pressure measurements of the sorbitan emulsifiers at the air-water interface (Wan, L. S. C. and Philip, F. S., 1974, Surface Films of Sorbitan Esters at the Air-Water Interface. I. Effect of Compression Rate On Surface Pressure/Area Isotherms of Sorbitan Esters. Canad. J. Pharm. Sci., 9(3):82). The tendency for the sorbitan triesters to stretch over the interface may form a cohesive membrane to retain the carrier vacuoles. Another factor could involve the common sorbitan moiety of sorbitan monostearate and the sorbitan triesters which may form a favorable association between the emulsifiers to synergistically enhance the molecular orientation at the interface to prevent carrier escape from the globules. Evidently a hydrophobic emulsifier which effectively encapsulates the carrier may do so by participating in stabilizing the milkfat-water emulsion. Blending emulsifiers by increasing the concentration of Span 60 produced maximum encapsulation between the ratios of 0.5 to 0.7. Greater amounts of Span 60 reduced the encapsulation.

In subsequent experiments, the glucose carrier was replaced with a hydrolyzed protein. A hydrolyzed protein (Peptone, Difco, Detroit, Mich.) was chosen as a model carrier solution since capsules for cheese may contain peptides and amino acids as substrates for an encapsulated enzyme. As a protein hydrolyzate, only 50 to 60% of the peptone dry weight was protein. Therefore, the weight of peptone encapsulated represented only 50 to 60% of the total solids actually encapsulated.

The emulsifier blending experiment was performed by blending Span 60 with Glycomul TS at various proportions and encapsulating peptone solutions by spray technique. The initial percent encapsulation of peptone was between 80 to 90% regardless of the emulsifier blending ratios. Excellent encapsulation with single emulsifiers suggested peptone enhanced encapsulation possibly by containing surface active peptides and amino acids.

The capsules containing peptone and various proportions of Span 60 and Glycomul TS were incubated at 32° C. to simulate a typical milk ripening temperature for cheese making. Encapsulation measurements after incubation indicated capsules were more stable containing slightly more Glycomul TS in the emulsifier blend between the ratio of 0.25–0.5. Again, blending emulsifiers may improve capsule stability by developing a synergistic association at the interface. A slight excess of Glycomul TS in the blend may confer additional stability by the bulkiness to expand over the interface.

In general, the percent encapsulation decreased the most during the first 30 minutes of incubation with less carrier being lost during the next 55 minutes incubation at 32° C. During the initial 30 minutes incubation period, the capsules were undergoing a temperature change from 16° to 32° C. where volume expansion of approximately 59 $mm^3$/gm milkfat was expected. This initial volume expansion can stretch the interfaces and cause carrier leakage. The capsules are reasonably stable at 32° C. as evidenced by minimal carrier loss with continued incubation at 32° C.

The phase volume is an important consideration for emulsion formation and stability. The volume of the carrier added to a weight of milkfat was of critical importance for efficient encapsulation. This variable was investigated by addition of increased volumes of a 2% glucose solution to milkfat to establish a range of carrier/milkfat ratios from 0.1 to 0.6 (v/w). The percent encapsulation was nearly identical for all carrier volumes. A constant percent encapsulation was reflected by a steady increase in the weight of glucose encapsulated with increasing carrier volume.

The maximum ratio of carrier/milkfat (v/w) was 0.6 since larger carrier volumes caused inversion of the emulsion which resulted in dispersion of milkfat globules.

The experiments with carrier volume were expanded to include varying the emulsifier concentration from 1 to 10% of the milkfat with each carrier/milkfat (v/w) ratio of 0.2, 0.4 and 0.6. Capsules were formed with a peptone carrier and the capsule stability to 32° C. was determined. The results indicated that increased emulsifier concentration increased the initial encapsulation with all carrier volumes. The capsule stability to 32° C. indicated that an inadequate amount of emulsifier cannot stabilize the expanded interfacial area and carrier is released. Likewise, excess emulsifier in the milkfat decreased the capsule stability to 32° C. which became more detrimental with decreasing carrier volume. The extreme example is almost total destruction of capsules formed with 10% emulsifier and a minimal carrier/-milkfat (v/w) ratio of 0.2. The excess emulsifier appears to become surface active and may expand the milkfat surface area exposed to water which simultaneously disrupts the carrier vacuoles. Microscopic examination confirmed carrier loss but not the expansion of the milkfat surface area.

Maximum stability to 32° C. was obtained with an emulsifier concentration between 2.5 to 4.0%. When these concentrations of emulsifiers were used, 10 mg protein/gm milkfat-emulsifier were encapsulated regardless of the initial carrier volume. Under these conditions, the most efficient capsules were formed with a carrier/milkfat (v/w) ratio of 0.2 which maximized the carrier encapsulated and minimized carrier loss.

Milkfat temperatures of 45° to 52° C. were used to maintain molten stearate emulsifiers. These temperatures could inactivate enzymes before encapsulation. The effect of the carrier/milkfat emulsion temperature on encapsulation and stability to 32° C. was evaluated. The emulsifiers were melted at 62° C. and this milkfat-emulsifier mixture was cooled to 32° or 45° C. while stirred before the carrier was added and the capsules formed. For comparison, capsules were made at the normal temperature of 52° to 55° C. There was no difference in the initial percent encapsulation or capsule stability to 32° C. when capsules were formed at various milkfat/emulsifier temperatures.

If the capsules have potential use in cheese making, they must be stable to the milk ripening temperature of 32° C. The capsules should be stable at least through the milk coagulation stage if they are to be effective in modifying cheese flavor. The following process conditions formed capsules with maximal stability at 32° C. The emulsifier blend should consist of 1.5% Span 60 with 1.5% Glycomul TS based on the milkfat weight. The carrier volume should not exceed 20% of the milkfat weight. The carrier solute should be less than 10% (w/v) and preferably a proteinaceous material rather than salts or carbohydrates. The carrier/milkfat-emulsifier emulsion temperature at 35° C. would minimize heat damage to the carrier. Capsules could be formed in dispersion liquid of water containing 0.01% Tween 60° at 16° C.

The concepts described in the foregoing examples have application to other phases of the food and dairy field.

For example, the enzyme of Example 1 or the glucose and hydrolyzed protein of Example 2 may be replaced with other carriers and substrates for encapsulation, such as hemoglobins; multiple enzyme systems; pyruvates plus yeast extracts; pyruvate-thiamine pyrophosphate plus MgSO$_4$ mixtures; basal media bacteria cells; media for control of pH; agents for adjustment of oxidation-reduction reactions; redox materials; and chemical agents.

The milkfat in the foregoing examples can be replaced with other food grade encapsulating materials, such as butterfat, animal fats, snythetic fats, vegetable oils (hydrogenated or unhydrogenated) and other oleaginous materials. The oleaginous encapsulating material selected should be fluid during emulsification of the aqueous phase in the oleaginous material.

The aqueous medium in which the emulsion is dispersed and which may be substituted for the skim milk in the foregoing examples includes, by way of example, water and other liquid systems such as gels, sols, beer, beverages and the like.

Carrier emulsification within small capsules requires extensive emulsification of the carrier in the encapsulating material. This can be accomplished by rapid stirring of the emulsion. It is sufficient to make use of a stirring rate which maintains a homogenous dispersion of the carrier in the milkfat or other encapsulating oleaginous material. The formed emulsion is best dispersed in the aqueous medium under high shear of the type readily developed with well known commercial emulsification and dispersion equipment.

In the foregoing examples, encapsulation of more than 90% of the carrier (including enzymes) was achieved in capsules of micro-dimension which remained stable over an extended period of time at temperatures below the melting point temperature of the fat component encapsulating the carrier, such as at a temperature of 32° C.

In the W/O emulsion, use can be made of a material to be encapsulated that is dispersible in the aqueous medium as well as a material that dissolves in aqueous medium, or mixtures thereof. The ratio by weight of aqueous component emulsified in the continuous phase of oleaginous material may be within the range of up to 0.6 but preferably within the range of 0.1–0.6. For emulsification, the two phases should be in a liquid state. This limits the emulsification to a temperature above the solidification temperature of the oleaginous material making up the continuous phase of the emulsion, and preferably at a temperature which is at least 5° C. and preferably 15° C. above the melting point of the oleaginous material but below the boiling point of the aqueous medium and below the temperature at which carrier materials may be subject to thermal decompositions.

For dispersion of the emulsion in the aqueous medium, it is desirable to make use of a temperature at which rapid solidification of the oleaginous carrier can take place and preferably at a temperature below that at which enzymes or other substrate to be encapsulated are destroyed. Best results are secured when the W/O dispersion is carried out with the phases at a temperature within the range of 16°–25° C. With most oleaginous materials capable of being used, it is undesirable to allow the temperature to exceed 35° C. while, at temperature below 16° C., solidification of the oleaginous material is too rapid with the result that the material disperses as large globules and not as particles of microdimension. The maximum temperature depends upon the thermal stability of the enzyme or other substrate but should be less than the boiling point for the aqueous medium of both the emulsified phase and continuous phase of the subsequently formed dispersion.

The weight ratio of W/O emulsion in aqueous dispersion liquid is not significant since it can be varied from as little as 1 to 100 parts by weight of W/O emulsion to 100 parts by weight of aqueous dispersion liquid and preferably within the range of 1-5 to 10.

As previously described, good results can be secured when use is made of 5% by weight hydrophobic emulsifying agent dissolved in the carrier phase but the amount can be varied in the range of 2–10% by weight of the fat phase to make use of a mixture of hydrophobic emulsifying agent.

In forming the dispersion of the W/O emulsion in the aqueous phase, a hydrophilic emulsifying agent dissolved in the aqueous medium serves no useful purpose when the aqueous dispersion liquid is skim milk or the like milk product. When formed of water or other aqueous solution, advantageous use can be made of a hydrophilic emulsifying agent dissolved in the aqueous dispersion liquid in an amount within the range of 0.01–1% by weight of the aqueous phase.

It will be apparent from the foregoing that means are provided for protecting enzymes or other substrates until it is desired to effect release into a localized, controlled environment. This enables release in intimate association with the reactive components to the end that, upon release, the encapsulated material is many times more effective by comparison with the addition of the same amount directly at the beginning of the process. When, for example, the enzymes are added directly to milk used in the processing of cheese, a large proportion of the enzymes are lost with the separated whey while the portion remaining with the curd is so diluted as to provide minimal effect. On the other hand, when encapsulated, for controlled release, little, if any, is lost in the separated whey, while the great majority of the capsules remain with the curd for subsequent release in an environment whereby the enzymes are 6 to 8 times more effective in their reaction for development of flavor and aroma.

Microencapsulation by way of a multiple phase emulsion, in accordance with the invention, yields particles of microdimension, such as within the range of 5–15 microns with the result that good distribution can be achieved of the encapsulated materials when used in the process industry in the preparation of food and dairy products.

It will be apparent that changes may be made in the details of formulation and operation without departing from the spirit of the invention, especially as defined in the following claims.

We claim:

1. A process for accelerating flavor production during cheese ripening comprising emulsifying an aqueous enzyme extract of cheese flavoring microorganism in a fluid oleaginous material-emulsifying agent mixture to produce a water-in-oil emulsion wherein the aqueous extract constitutes the discontinuous phase dispersed within a continuous phase of fluid oleaginous material, dispersing the resulting emulsion in milk to form a suspension of oleaginous microcapsules containing the aqueous extract dispersed therein, coagulating the resultant milk containing suspended microcapsules to produce a cheese curd, and curing the curd to produce cheese containing flavors generated by the extract of the cheese flavoring microorganisms contained by the microcapsules.

2. The process as claimed in claim 1, in which the oleaginous material contains a hydrophobic emulsifying agent dissolved therein in an amount within the range of 1-10% by weight.

3. The process as claimed in claim 1, in which the emulsifying agent has an HLB below 6.

4. The process as claimed in claim 1 in which the emulsifying to form the water-in-oil emulsion is carried out at a temperature at least 5° C. above the melting point temperature of the oleaginous material.

5. The process as claimed in claim 1 in which the emulsifying to form the water-in-oil emulsion is carried out at a temperature of 15° C. above the melting point temperature of the oleaginous material but less than the boiling point temperature of the aqueous component.

6. The process as claimed in claim 1 in which the milk contains an emulsifying agent having an HLB within the range of 8-18.

7. The process as claimed in claim 6, in which the emulsifying agent is present in the milk in an amount within the range of 0.01-1% by weight.

8. The process as claimed in claim 1, in which the dispersing of the emulsion is carried out at a temperature below the melting point temperature of the oleaginous material.

9. The process as claimed in claim 1, in which the dispersing of the emulsion in the milk is carried out at a temperature within the range of 16°-32° C.

10. The process as claimed in claim 1, in which the emulsifying agent is a blend of emulsifying agents, one of which has an HLB below 4 and another of which has an HLB within the range of 4 to 8.

11. The process as claimed in claim 1 in which the aqueous enzyme extract and oleaginous material are present in an amount of 1-5 parts by weight aqueous enzyme extract to 10 parts by weight oleaginous material.

12. A process for producing cheese, having an increased content of diacetyl and acetoin, comprising emulsifying an aqueous enzyme containing cell free extract from the microorganism Streptococcus lactis. subsp. diacetilactis in a milk fat-emulsifier mixture to produce a water in oil emulsion wherein the aqueous cell free extract constitutes a discontinuous phase dispersed within a continuous phase of milk fat, dispersing the resultant emulsion with agitation into skim milk to form a suspension of milk fat microcapsules containing the cell free extract dispersed therein, coagulating the resultant skim milk containing suspended microcapsules to produce a cheese curd, and curing the curd to produce cheese containing diacetyl and acetoin generated by the enzymes in the cell free extract contained by the milk fat microcapsules.

13. The process as claimed in claim 12, in which the emulsifying to form the water-in-oil emulsion is carried out at a temperature above 35° C. but below the temperature at which the enzymes would be destroyed.

14. The process as claimed in claim 12, in which the emulsifier is a mixture of a trisorbitan fatty acid, and a monosorbitan fatty acid.

15. The process as claimed in claim 12, in which the emulsifier is triglycerol mono-di or tri fatty acid and a sorbitan mono-di or tri fatty acid.

16. The process as claimed in claim 14, in which the fatty acid is a stearate or oleate.

17. The process as claimed in claim 12 which includes the step of cooling the water-in-oil emulsion to a temperature within the range of 16°-35° C. before dispersion in the skim milk.

18. The process as claimed in claim 12, in which the aqueous cell free extract/milk fat-emulsifier mixture is within the range of 1-100 parts by weight aqueous cell free extract per 100 parts by weight milk fat-emulsifier mixture.

19. The process as claimed in claim 12, in which the emulsifier is within the range of 2-10% by weight of the oleaginous component.

* * * * *